(12) United States Patent
Ferreira et al.

(10) Patent No.: US 11,344,647 B2
(45) Date of Patent: May 31, 2022

(54) WIRELESS ELECTROMECHANICAL DEVICE FOR CONTROLLED RELEASE OF FRAGRANCES AND SCENTS

(71) Applicants: PANAPANAS INC. LTD., Nassau (BS); Cláudia Galvão, São Paulo-SP (BR)

(72) Inventors: Tulio Silvio Ferreira, Pará de Minas (BR); Cláudia Galvão, São Paulo-SP (BR)

(73) Assignees: PANAPANAS INC. LTD., Nassau (BS); Cláudia Galvão, São Paulo (BR)

( * ) Notice: Subject to any disclaimer, the term of this patent is extended or adjusted under 35 U.S.C. 154(b) by 198 days.

(21) Appl. No.: 16/621,979

(22) PCT Filed: Oct. 10, 2018

(86) PCT No.: PCT/BR2018/050319
§ 371 (c)(1),
(2) Date: Dec. 12, 2019

(87) PCT Pub. No.: WO2020/073104
PCT Pub. Date: Apr. 16, 2020

(65) Prior Publication Data
US 2021/0361813 A1    Nov. 25, 2021

(51) Int. Cl.
*A61L 9/14* (2006.01)
*B05B 12/02* (2006.01)

(52) U.S. Cl.
CPC .............. *A61L 9/14* (2013.01); *B05B 12/02* (2013.01); *A61L 2209/11* (2013.01); *A61L 2209/134* (2013.01)

(58) Field of Classification Search
None
See application file for complete search history.

(56) References Cited

U.S. PATENT DOCUMENTS 5,268,214 A    12/1993  Charbonneau
9,137,186 B2    9/2015  Tange
(Continued)

FOREIGN PATENT DOCUMENTS

BR          9206449 A    11/1994
WO     2013001972 A1     1/2013
(Continued)

OTHER PUBLICATIONS

Merriam-Webster Dictionary: "Cotter Pin" Definition, [online] [retrieved on Nov. 3, 2021] https://www.merriam-webster.com/dictionary/cotter%20pin (Year: 2021).*

(Continued)

*Primary Examiner* — Jelitza M Perez
(74) *Attorney, Agent, or Firm* — Maier & Maier, PLLC

(57) ABSTRACT

An electromechanical emitter of fragrances/scents includes a blowpipe constructed in elastomeric material, which has an open edge layered by a latch valve and the other edge, closed, contains a magnet. In the internal side of the blowpipe, there is an absorber element with the fragrance or scent and an electric reel curly in its external side. When the reel receives alternated electric pulses, it generates a form of magnetic inductance shaping an alternated magnetic field attracting and repelling the magnet, making the blowpipe to enter into a frequency where a greater range of movement and greater volume of air in motion through the internal side of the system can be observed, enhancing the scent during the blowpipe vibration.

5 Claims, 5 Drawing Sheets

(56) References Cited

U.S. PATENT DOCUMENTS

| | | | |
|---|---|---|---|
| 2014/0189026 A1* | 7/2014 | Tange | H04L 51/10 |
| | | | 709/206 |
| 2015/0019030 A1 | 1/2015 | Chandler et al. | |
| 2015/0048178 A1 | 2/2015 | Edwards et al. | |
| 2017/0274405 A1* | 9/2017 | Lucas | A61L 9/14 |
| 2017/0282201 A1 | 10/2017 | Ben-David et al. | |
| 2017/0368219 A1 | 12/2017 | Li | |

FOREIGN PATENT DOCUMENTS

| | | |
|---|---|---|
| WO | 2017100874 A1 | 6/2017 |
| WO | 2018102893 A1 | 6/2018 |

OTHER PUBLICATIONS

International Search Report and Written Opinion, with English translation, dated Mar. 20, 2019, in corresponding International Application No. PCT/BR2018/050319, 15 pages.

* cited by examiner

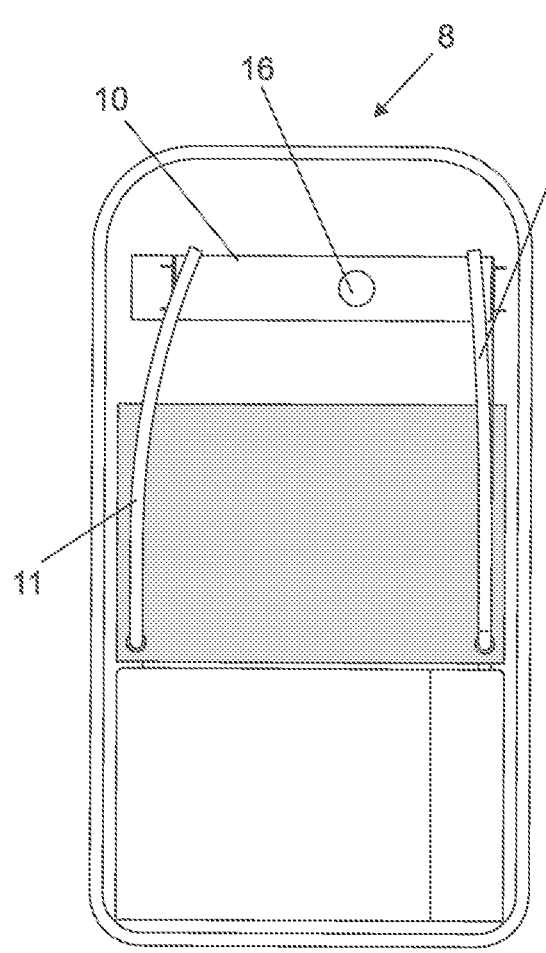
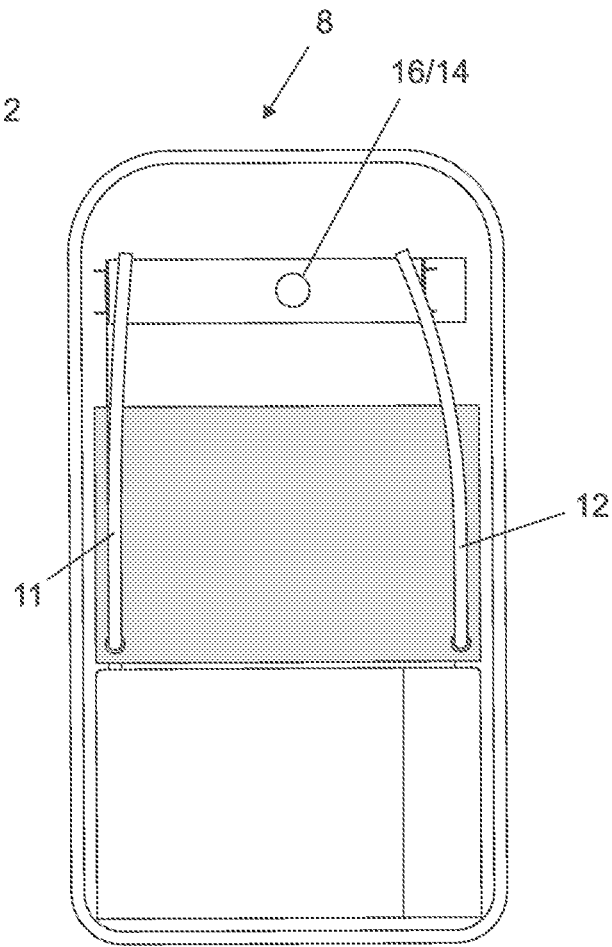
FIG.5A  FIG.5B
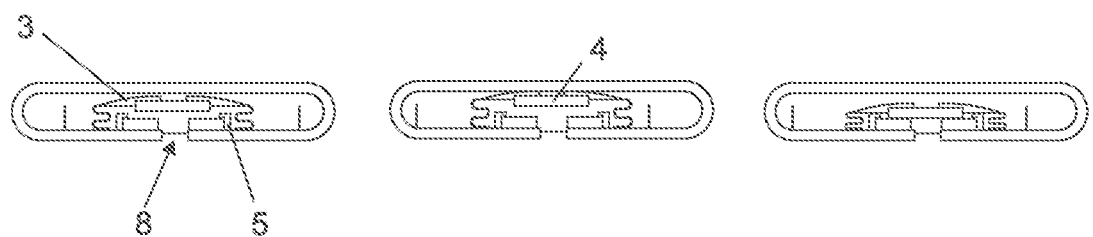
FIG.6A  FIG.6B  FIG.6C

WIRELESS ELECTROMECHANICAL DEVICE FOR CONTROLLED RELEASE OF FRAGRANCES AND SCENTS

FIELD

This patent application of invention belongs to the sector of sampling and testing of fragrances or scent and applies to an original device capable to release perfumed or aromatized air, offering to the user, an accurate scent experience. The device is composed by an integrated circuit, electromechanical emitter (blowpipe and reel) and fragrance or scent reservoir. It is activated via wireless command, originating from an application installed on tablet, smartphone, or notebook and in seconds, releases the fragrance or scent for the user's appreciation.

BACKGROUND

The current technique status, anticipates some patents documents related to devices providing fragrances and scents, such as WO2018/102893 A1—used in the testing sector of fragrances and scents as showcase, and it is enabled by an electrothermal system adjusted by a set of conductors, interconnected by resistors printed on a holder located in the internal side of the fragrance deposit. Once actuated, via wireless, the electrothermal system disperses and releases the fragrance. The compartments for fragrance and scent deposit are free or semi-sealed shafts.

The solution above disfigures the fragrances/scents as uses an electrothermal system, and as the fragrances/scents are composed by several chemical substances, some of them highly volatile that are lost and/or disfigured at the very first heating of the system. The following heating(s) exacerbate the loss detrimentally to the future scent experiences, due to the vaporization of the most volatile "scent notes." Therefore, such solution, presents technical effect and positive details different from the device herein claimed. Likewise, the activation via wireless for this application is not new, as can be verified in the coming anteriority.

WO2017/100874 A1—is a device used in digital electronic catalog of fragrance/scent replacing the printed catalog. It operates associated to an application for mobile device, tablet, notebook, desktop or even in proprietary control, which by means of wireless communication activates the refills with the microcapsules of fragrances/scents that are exhaled by the temperature increase. The system is supplemented by fans and a fabric located in the intersperse of the release mechanism, the resistance, and the perforated screen.

The device of this anteriority also uses the heating of the fragrance/scent to produce vapors with the purpose to provide scent testing for the user. However, the heating of fragrances/scents brings the same inconveniences described in the previous document, meaning, the scent disfigurement. This anteriority anticipates the use of wireless to activate the device, besides to use fans and a fabric to optimize the scent exhalation.

US2015/0048178—This is a system controlled to provide scent sensations to one or more users. The scent release can be activated by sound, synchronized to an image from a unit of actioning, which can be or cannot be controlled by the user. The system is composed by a set of cartridges of scent, tubes, circuits, valves, and fans.

The US document presents the disadvantage of not being "wireless", as it is composed by two modules connected by cables. It also features the same inconveniences quoted in the previous topics, as it heats the fragrances or scents. There is also the disadvantage of being an equipment with much larger dimensions compared to the device now claimed and be divided in two modules, making difficult to use it. There are much more mechanical parts, such as fans and tubes. Another bound is on the circulation of liquids by the tubes, which can cause unwelcome leaking and spills.

PI9206449—Concerns the application method of microcapsules with fragrances, protected by a substratum, to papers to be used as fragrances sampling.

The method described in the document above presents limitations and inconveniences, such as: excessive spent of paper in the making of the catalogs and the non-automation and miniaturization of the elements involved in the scent experience.

WO2013/001972—Concerns the release system of fragrances activated by the receipt of an electronic message (via e-mail, for example). When receiving the message, the system activates the fragrance emitter unit and the user smells it.

The WO above demonstrates a device that releases fragrances applied to devices of messages exchange, which emit according to messages received via internet, however there is the disadvantage to require a physical connection with the device that generates the signal. The system is not miniaturized.

SUMMARY

The purpose of this invention is to propose a wireless electromechanical device for controlled release of fragrances and scents, where the activation by means of alternated insufflation makes the fragrances/scents to maintain its original features, as they do not suffer the action of elements that can alter them, as in the electrothermal activation devices. It is known that the heating of the fragrance/scent disfigures the smell, as in the very first heating, highly volatile compound (vaporize prior than the others) are lost. A fragrance is composed by many chemical substances and each one with a different boiling point (vaporization).

The purpose of this invention is to propose a wireless electromechanical device for controlled release of fragrances and scents, capable to offer a unique scent experience to the user to evaluate a fragrance or scent in place of glass jars, scent tapes, and equipment that heat and disfigure the fragrances.

The purpose of this invention is to propose a wireless electromechanical device for controlled release of fragrances and scents, whose operating principle enables the saving of fragrances or scents, as the device does not pulverize, fog, and neither heats the fragrances and scents.

The purpose of this invention is to propose a wireless electromechanical device for controlled release of fragrances and scents that solves the disability of other equipment, which pulverize or fog the fragrances or scents, as this technique contaminates the surfaces of the emitter device itself, leaving it impregnated with the residual smell, and the consequent loss of function of the emitter, only when receives such command. This device presents the advantage that only the air passes by the fragrance or scent reservoir and this air carries the smell that will reach the user's sense of smell.

The purpose of this invention is to propose a wireless electromechanical device for controlled release of fragrances and scents capable to generate a greater saving of fragrances or scents, as there is not waste with nebulization or pulverization, which requires higher volumes. There is also the saving of glass jars used to demonstrate the perfumes, as well as paper tapes, such as olfactive tapes.

The purpose of this invention is to propose a wireless electromechanical device for controlled release of fragrances and scents with a compact size when compared to the existing devices, that besides not having the same principle of fragrance or scent emission, are also much larger than the device now claimed.

The purpose of this invention is to propose a wireless electromechanical device for controlled release of fragrances and scents capable to perform a great number of shots to demonstrate and appreciate the fragrances and scents and is also capable to replace the traditional glass jars with the capacity of 3 ml of fragrances.

The purpose of this invention is to propose a wireless electromechanical device for controlled release of fragrances and scents capable to foster the user with a unique and accurate scent experience, as soon as the user sends a wireless command from a tablet, cell phone or notebook.

The WIRELESS ELECTROMECHANICAL DEVICE FOR CONTROLLED RELEASE OF FRAGRANCES AND SCENTS is a technological platform inclusive of systems with several purposes, including an electromechanical emitter, effected by means of blowpipe or membrane, and transmitter/receiver of radio frequency for controlled release of fragrances and scents, activated by an electronic signal commanded by wireless communication.

The operation of the device is simple, the air aromatization is made with the vacuum of the outside air to the internal side of the device, where it passes through a cell containing the fragrance or scent and after the perfumed or aromatized air is expelled from the device in an alternating flow of entry and exit of small quantities of air, several times and for some seconds, enabling an immediate experience in a single dose to the experimenter.

BRIEF DESCRIPTION OF THE DRAWINGS

Follow-up, the figures for a better explanation of the patent application are presented, in an illustrative and non-limiting form:

FIG. 5A: Front view of the emitter element of wireless electromechanical device for controlled release of fragrances and scents, illustrating the latch valve sealing the fragrance/scent passage to the external environment.

FIG. 5B: Front view of the emitter element of the wireless electromechanical device for controlled release of fragrances and scents, illustrating the latch valve releasing the fragrance/scent passage to the external environmental.

FIG. 6: Side view of the emitter element of the wireless electromechanical device for controlled release of fragrances and scents, showcasing the blowpipe static (6A), the powered circuit with the blowpipe in its greater opening (6B) and the blowpipe in its smaller opening (6C).

DETAILED DESCRIPTION

Figure 1:
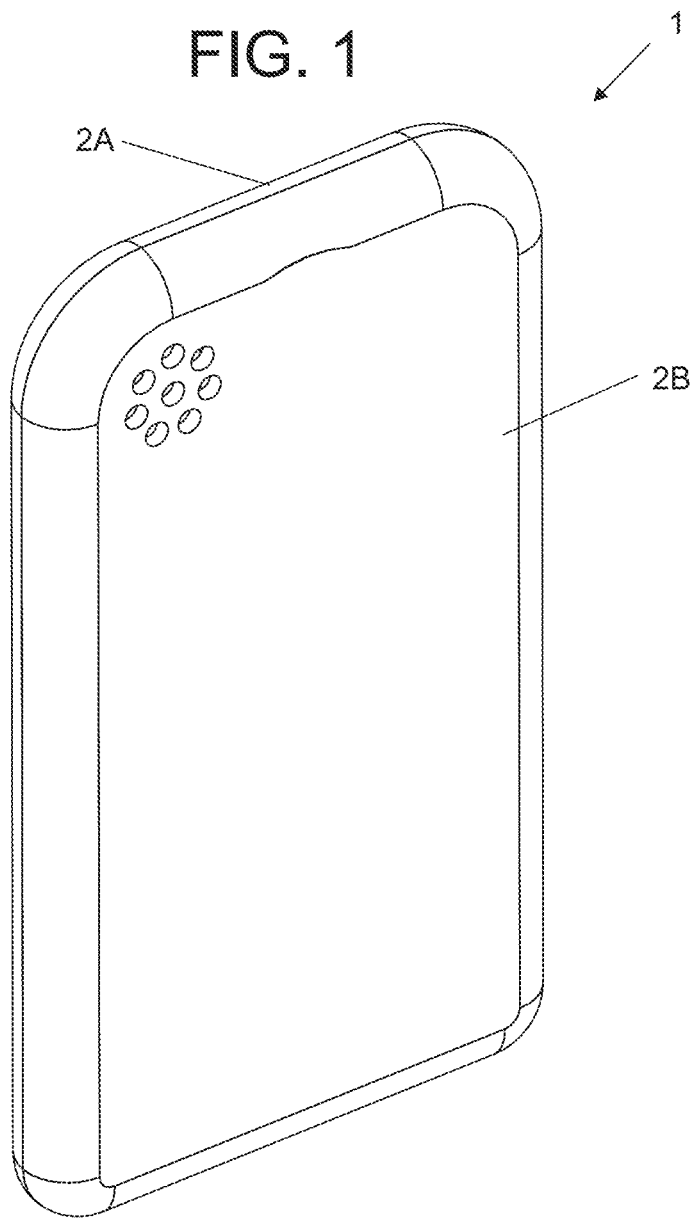
FIG. 1: View in perspective of the wireless electromechanical device for controlled release of fragrances and scents.

The WIRELESS ELECTROMECHANICAL DEVICE FOR CONTROLLED RELEASE OF FRAGRANCES AND SCENTS is an electromechanical emitter of fragrances/scents (1), composed by a blowpipe (3) constructed in elastomeric material, which has an open edge layered by a latch valve (8) and the other edge, closed, by a magnet (4). In the internal side of the blowpipe (3), there is an absorbing element (7) with the fragrance or scent and an electric reel (5) curly in its external side. When the reel (5) receives alternated electric pulses, it generates a form of magnetic inductance shaping an alternated magnetic field, attracting and repelling the magnet (4), making the blowpipe (3) to enter a frequency where it is possible to observe the greater range of movement and greater volume of air in motion through the internal side of the system, intensifying the scent during the blowpipe (3) vibration.

Notably, the electromechanical emitter of fragrances/scents (1) is constructed of a two-part casing (2A and 2B), which endures an electromechanical system (S) of alternated insufflation, represented by a blowpipe (3) properly activated by a set of magnet (4)/reel (5), supplied by means already known, in this mode of viability of the invention by a battery (6), in what way when inflates air into the direction of the absorbing element (7), routes the fragrance or scent in it to the external environment, without any kind of loss of scent quality. A latch valve (8) completes the emitter, with the purpose to prevent the overflow of the fragrance when the product is not being used.

Figure 2:
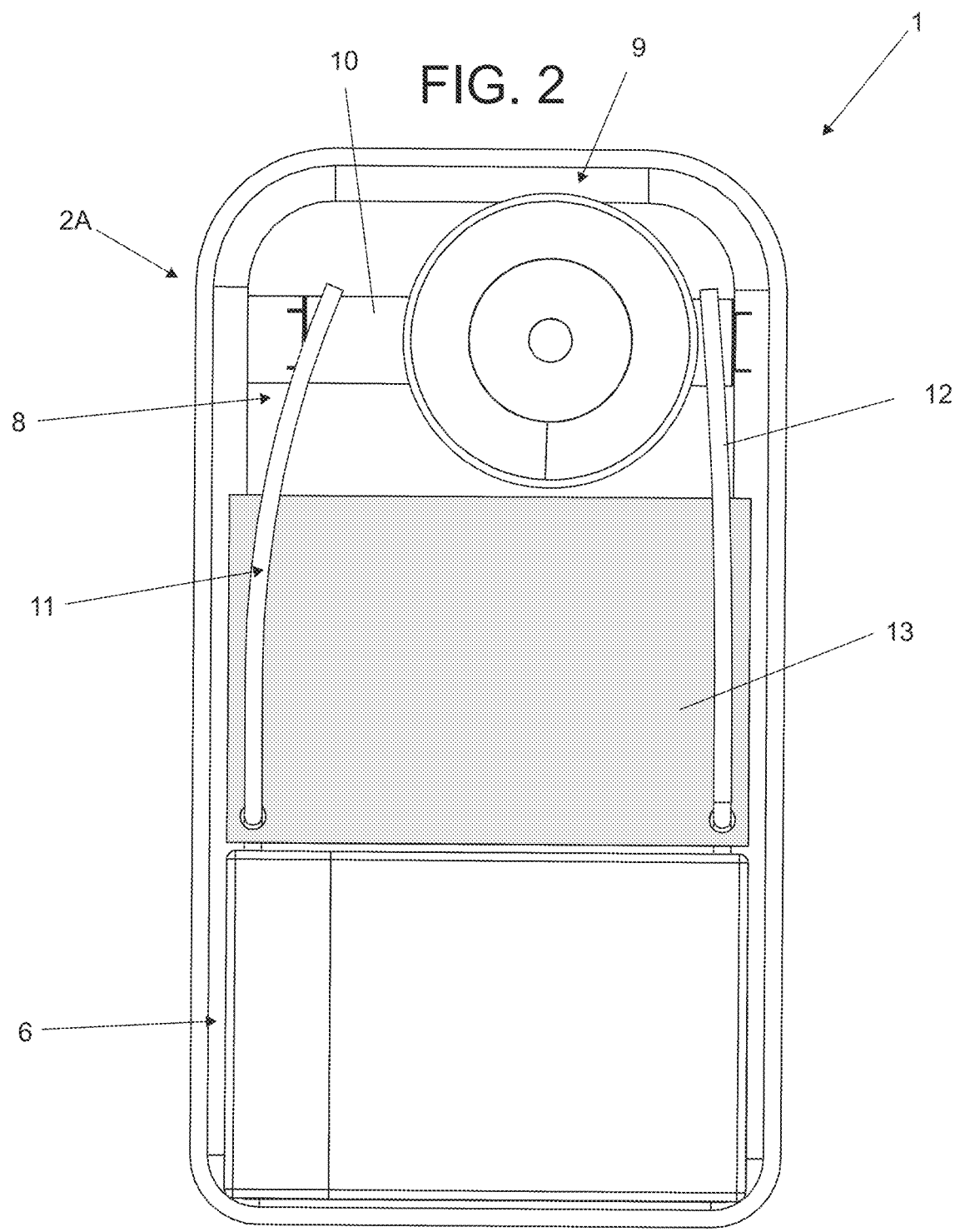
FIG. 2: Front view of the wireless electromechanical device for controlled release of fragrances and scents with the casing open.

As illustrated at FIG. 2, the electronic emitter of fragrances/scents (1) is composed by the emitter element (9), allocated in the medium center of the casing (2A), and also a latch valve (8) set by drilled blade (10) and two wires (11 and 12) made of distinct material, which move horizontally, by a potential difference produced in the electronic circuit board (13), in which they are connected. The electromechanical emitter of fragrances/scents (1) is supplied by battery (6), located under the circuit board (13).

Figure 3:
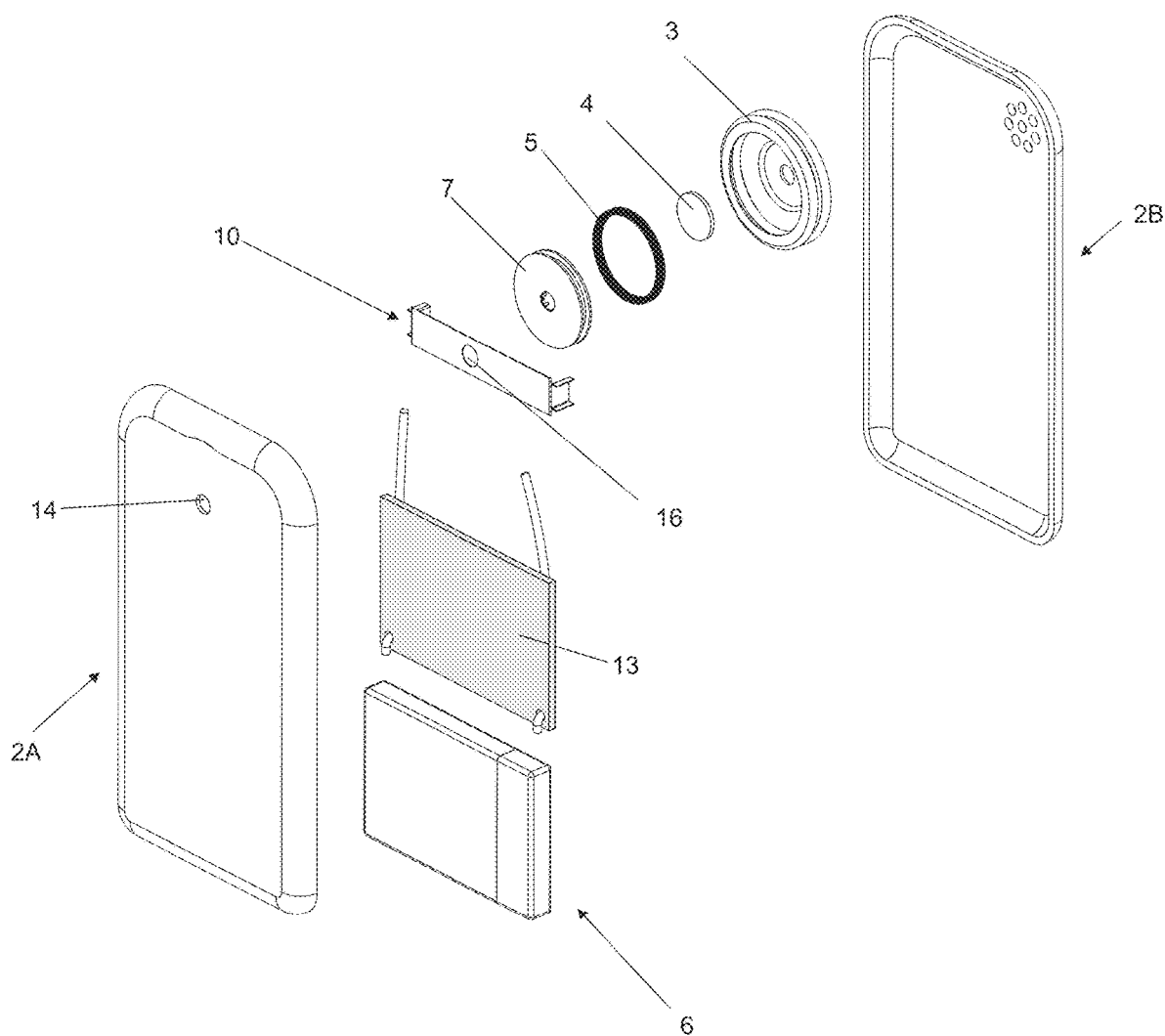
FIG. 3: View in exploded perspective of the wireless electromechanical device for controlled release of fragrances and scents.

As illustrated at FIG. 3, the casing is in two parts (2A and 2B), which are complementary and fit to each other, and at the medium higher point of the part (2A), a hole (14) excels for the exit of fragrances/scents. Internally to the casing (2A), a rail (15) is stated for the linear movement of the drilled blade (10) of the latch valve (8), as already noted, whose movement is made by the potential difference of the Nitinol wire (11) and the stainless-steel wire (12), or other material that complies with the needs of return of the latch valve (8). On the subject, the fragrances/scents will only be overflowed to the environment when there is the coincidence of the hole (16) of the drilled blade (10) with the hole (14) of the casing (2A) and when the blowpipe (3), magnet (4) and reel (5) inflate the air alternately through the absorbing element (7).

Figure 4:
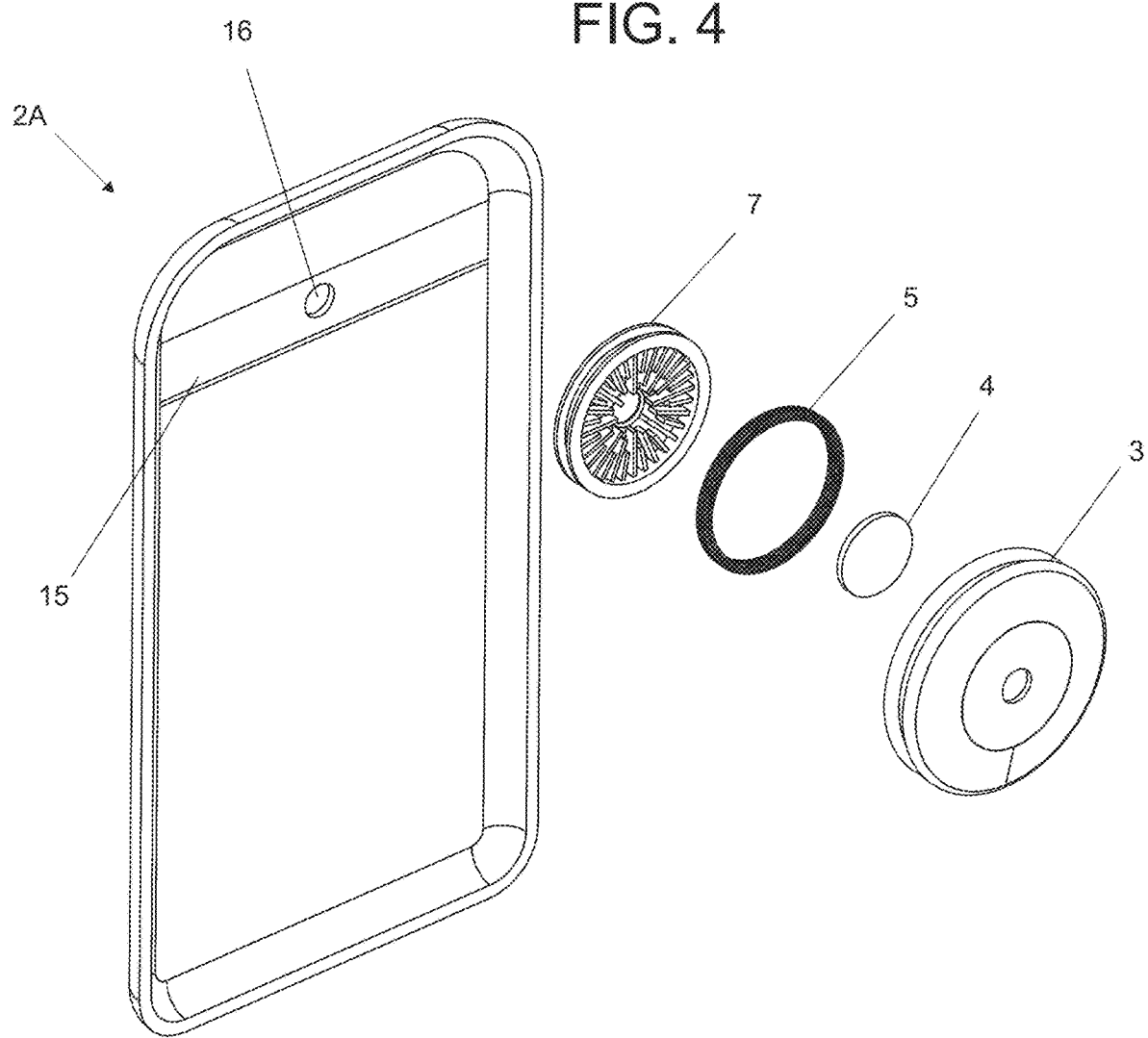
FIG. 4: View in exploded perspective of the emitter element of the wireless electromechanical device for controlled release of fragrances and scents

At FIG. 4, it is possible to observe with a greater precision the electromechanical system of alternated insufflation of air, represented by the blowpipe (3), magnet (4) and reel (5), as well as the absorbing element (7), the rail (15) and the hole (14) in the casing (2A). At FIGS. 5A and 5B, the operation of the latch valve (8) is demonstrated. At FIG. 5A, the Nitinol wire (11) that has a great mechanical memory, is curved to the right, as the electromechanical emitter of scents (1) is disconnected, while the stainless-steel wire (12) is rectilinear. In this condition, the hole (16) of the drilled blade (10) and the hole (14) of the casing (2A) are into different directions, therefore, sealing the passage of fragrance/scent to the external environment. At FIG. 5B, with the electromechanical emitter of scents (1) powered, the Nitinol wire (11) heats and takes a vertical straight position forcing the twist of the stainless-steel wire (12) and the movement of the drilled blade (10), which runs across the rail (15) to the left side leading to the compliance between the hole (16) of the drilled blade (10) and the hole (14) of the casing (2A). In this condition, it gives passage for the fragrance/scent to the external environment.

As illustrated at FIG. 6, the operation of the electromechanical system, notably the blowpipe (3), magnet (4) and reel (5) allocated on the absorbing element (7) follows a logic sequence (6A, 6B, 6C). At FIG. 6A, the blowpipe (3) is static, as the electromechanical emitter of scents (1) is disconnected, therefore the latch valve (8) is sealed (unpowered), the reel (5) disconnected and without any insufflation of air into the system. At FIG. 6B, with the electromechanical emitter of scents (1) connected, the latch valve (8) is giving passage (powered), meaning, the Nitinol wire (11) is curling the stainless-steel wire (12) to make the hole (16) of the drilled blade (10) and the hole (14) of the casing (2A) coincide. The Reel (5) is connected for inductive force of repulsion, acting in conjunction with the magnet's (4) magnetic force of repulsion, in this condition the blowpipe is full of air. At FIG. 6C, still with the electromechanical emitter of scents (1) connected, the latch valve (8) is giving passage, however, the polarity of the reel (5) reverses and the magnet maintains the attraction force, in what way in this condition the blowpipe insufflates the air through the absorbing element (7), exhaling the fragrance through the hole (14) and so on continuously.

The number of cycles of entry and exit of air in the device, or the time of each experience is controlled by the circuit board empowered with a configurable chip to obtain the scent experience and the aimed result.

The invention claimed is:

1. A fragrance release device, comprising:
a battery;
a circuit board allocated in a casing in two-parts with a hole, where outside air enters and fragrances/scents exit by wireless command via an application from a tablet, a cell phone or a notebook, wherein a release of fragrances/scents is through an electromechanical system of alternated insufflation, represented by a blowpipe, activated by a magnet and a reel; in an internal side of the blowpipe there is an absorber element with the fragrance or scent and the reel curly in its external side; the reel receives alternated electric pulses and generates magnetic inductance, shaping an alternated magnetic field, attracting and repelling the magnet, making the blowpipe enter into a frequency where a greater range of movement and greater volume of air in motion through the internal side of the blowpipe can be observed, enhancing the scent during blowpipe vibration; and
a latch valve under the open surface of the blowpipe completes the electromechanical system.

2. The device according to claim 1, wherein the latch valve is configured by a drilled blade, which moves in a rail, and two wires made of distinct materials, which move horizontally, by a potential difference produced in the circuit board, where they are connected.

3. The device according to claim 1, wherein the latch valve is closed when the circuit board is unpowered, a Nitinol wire remains curved, obliging disagreement between a hole of a drilled blade and the hole of the casing.

4. The device according to claim 1, wherein the latch valve is opened when the circuit board is powered, a Nitinol wire returns to an original position obliging compliance between a hole of a drilled blade and the hole of the casing.

5. The device according to claim 1, wherein the electromechanical system comprises the blowpipe, the magnet, the reel and the absorber element.

\* \* \* \* \*